(12) United States Patent
Italiano et al.

(10) Patent No.: US 7,687,029 B2
(45) Date of Patent: Mar. 30, 2010

(54) AUTOMATED ANALYSER FOR DETERMINING NITROGEN DERIVED FROM ORGANIC COMPOUNDS

(75) Inventors: Pietro Italiano, Vignate (IT); Bruno Lavettre, Valencia, CA (US)

(73) Assignee: Ecoenergetics S.r.l., Milan (IT)

( * ) Notice: Subject to any disclaimer, the term of this patent is extended or adjusted under 35 U.S.C. 154(b) by 1276 days.

(21) Appl. No.: 11/106,996

(22) Filed: Apr. 15, 2005

(65) Prior Publication Data

US 2005/0266580 A1 Dec. 1, 2005

(30) Foreign Application Priority Data

Apr. 15, 2004 (IT) .................. MI2004A000740

(51) Int. Cl.
*G01N 31/12* (2006.01)
(52) U.S. Cl. .................. 422/78; 422/68.1; 422/82.01; 422/83; 422/88; 422/98
(58) Field of Classification Search ................ 422/68.1, 422/78, 80, 81, 82.01, 83, 88, 90, 98
See application file for complete search history.

(56) References Cited

U.S. PATENT DOCUMENTS

| | | | | |
|---|---|---|---|---|
| 5,612,225 A | * | 3/1997 | Baccanti et al. | 436/114 |
| 5,866,072 A | * | 2/1999 | Bowe et al. | 422/78 |
| 6,321,609 B1 | * | 11/2001 | Mengel et al. | 73/863.21 |

* cited by examiner

*Primary Examiner*—Jill Warden
*Assistant Examiner*—Dwayne K Handy
(74) *Attorney, Agent, or Firm*—Collard & Roe, P.C.

(57) ABSTRACT

An automated analyzer is described for determining, by way of combustion, nitrogen contained in organic compounds, in particular proteins present in foods, animal feeds, polymers, fuels etc., characterized in that the carbon dioxide absorption device upstream of the nitrogen detector is self-regenerating and comprises:
 a distributor valve able to switch different gas circuits without contaminations and losses from one gas sample to another,
 a carousel consisting of a plurality of absorber elements inside which is placed an adsorbent material,
 a furnace suitable for said adsorbers,
in such a manner that each of said adsorbers presents itself in turn for each analysis and that on completion of said analysis the same adsorber is conveyed to the furnace for degassing of the absorbent material and thus for its relative regeneration.

21 Claims, 7 Drawing Sheets

FIG. 2
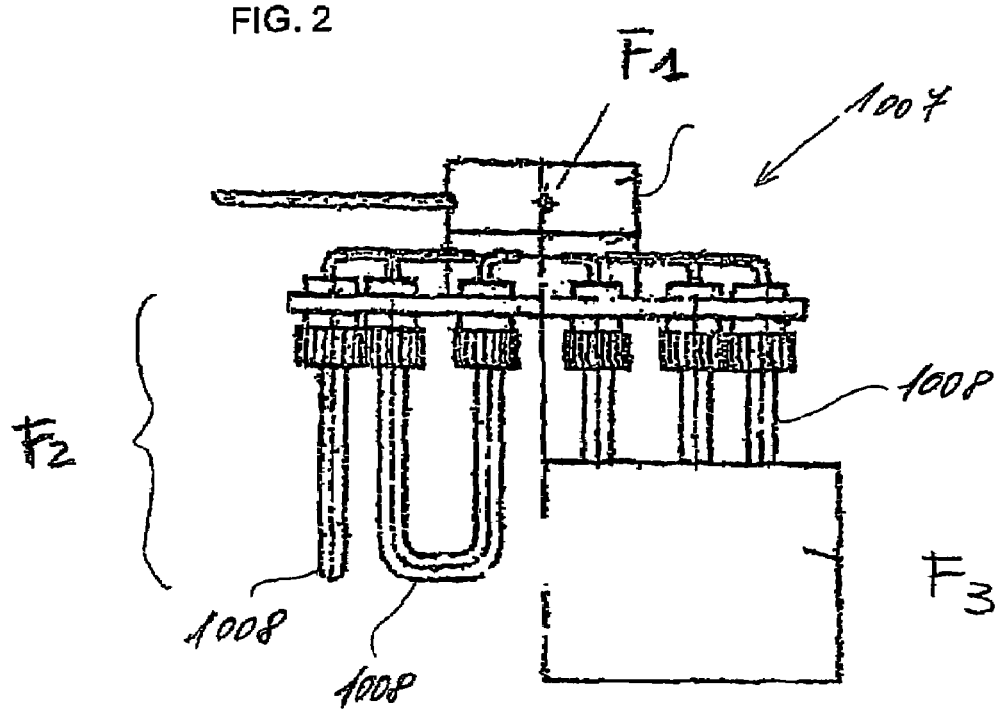
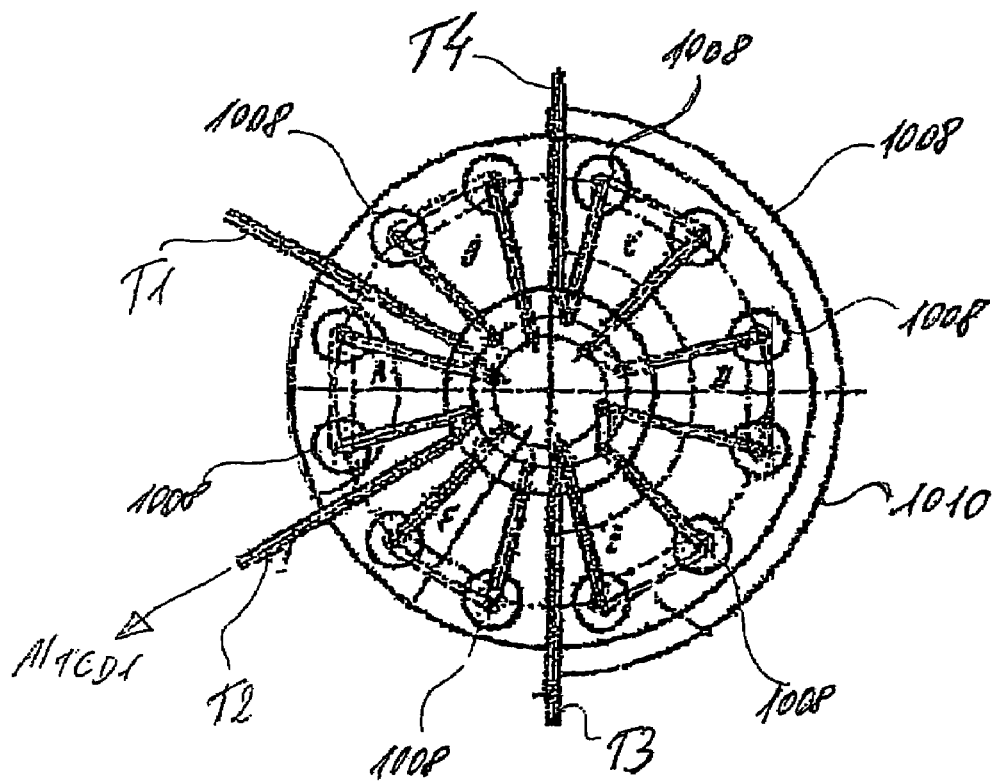
FIG. 2A

AUTOMATED ANALYSER FOR DETERMINING NITROGEN DERIVED FROM ORGANIC COMPOUNDS

FIELD OF THE INVENTION

The present invention relates to an automated analyser, by way of combustion, for determining nitrogen contained in organic compounds present in foods, animal feeds, polymers, fuels etc.

STATE OF THE ART

The determination of nitrogen content based on reduction to ammonia and subsequent titration was applied for the first time by Kjeldahl at the end of nineteenth century.

This method presents a number of operative drawbacks related to the use of sulfuric acid and pollutant catalysts, with the consequent problems of disposing of toxic residues, especially in cases where the aforesaid analysis must be conducted daily on a large number of samples.

The other method for determining nitrogen devised by Dumas is based on the technique of combustion or oxidation of the nitrogen contained in the organic compound using oxygen to form the various nitrogen oxides, which are subsequently reduced to nitrogen.

This method is used in the food industry as it is rapid, gives accurate measurement and is also more easily automated.

However, this technique involves a series of problems related to the combustion itself and to the fact that, during combustion, in addition to nitrogen formation, large amounts of carbon dioxide and water are also formed which have to be removed, via the insertion of traps or adsorbers, before the gaseous mixture passes to the nitrogen measurement instrument.

Initially, homogeneous gas phase combustion was used which is slower, however, and involves the presence of combustion support well over the stoichiometric amount.

Moreover, with this type of combustion, massive quantities of pyrolysis residues in the form of powders are formed. The products of combustion and the mixture with large combustion support excesses have to be collected and homogenized to proceed to the analysis, and of these only a small fraction passes to the analyser. Heterogeneous phase combustion in the presence of a solid phase catalyst has the advantage of being able to accelerate combustion using a smaller amount of combustion support. Indeed, in this type of combustion 0.3 g of organic substance can be burnt using 400 ml of oxygen in 30 seconds rather than the 8 litres in over 1 minute used in homogeneous combustion.

Analysers of this type are already commercially available, using heterogeneous phase combustion.

For example, with the Flash EA® 1112-Thermo Quest, the sample to be analysed is dropped into the heterogeneous combustion reactor in the presence of oxygen. In this phase the temperature of the oxidation reactor passes from 900 to 1800° C. as a consequence of oxygen intake, and the carbon and the hydrogen contained in the organic substance oxidise to carbon dioxide and water. In this phase the nitrogen is oxidised to $N_xO_y$. The gaseous mixture containing carbon dioxide, water and $N_xO_y$ is conveyed to the reduction reactor where the aforesaid nitrogen oxides are reduced to nitrogen. Subsequently the gases leaving the reduction reactor are conveyed to the carbon dioxide and water traps by the carrier gas helium. The gas leaving the water trap, consisting mainly of nitrogen, is fed to the analyser itself which consists of a gas chromatography column and a thermal conductivity detector (TCD or HWD—hot wire detector).

The detector is then connected to a logic unit for data processing.

Although these instruments demonstrate considerable advantages in that they are completely automated systems, they also present a number of drawbacks.

For example the carbon dioxide traps, generally of zeolite, must be replaced frequently to be regenerated, as they become saturated with carbon dioxide in the long term.

To overcome these types of problem, large traps are used which clearly have much longer saturation periods. However, the use of large traps involves considerable pressure drops in the gas flow as the gas flow has to pass through them, leading to errors in the final nitrogen measurement.

Another source of pressure drop in the system is caused by the presence of water traps generally consisting of inorganic compounds able to selectively absorb it, through which the gaseous fluid has to pass. This type of trap also tends to become easily saturated hence leading to frequent replacement with stoppage of the analyser.

In addition, they are unable to completely remove water, which reflects negatively on the final nitrogen measurement. Moreover, the very rapid heterogeneous combustion does not allow carbon to completely oxidise to $CO_2$ but only to CO, which, when it arrives at the detector, can result in erroneous assessments of the actual nitrogen content in the sample to be analysed.

The need was therefore felt for an analyser which would not present the aforesaid drawbacks.

SUMMARY OF THE INVENTION

The present invention provides an automatic analyser, by way of combustion, for the determination of nitrogen in organic compounds, in particular proteins present in foods, animal feeds, polymers, fuel etc., comprising:
  lines for gaseous fluids
  sample holders for analysis
  catalytic combustion reactor
  reduction reactor
  water adsorber
  $CO_2$ adsorber
  nitrogen detector
  logic unit for processing the determined data characterised in that the device for absorption of carbon dioxide is located upstream of the nitrogen detector, is self regenerating and comprises:
  a distributor valve able to switch different gas circuits without contaminations and losses from one gas sample to another,
  a carousel consisting of a plurality of absorber elements inside which is placed an adsorbent material,
  a furnace suitable for said adsorbers, in such a manner that each of said absorbers presents itself in turn for each analysis and that on completion of said analysis the same adsorber is conveyed to the furnace for degassing of the absorbent material and thus for its relative regeneration.

This avoids the use of large adsorbers which lead to considerable pressure drops in the gaseous fluid to be analysed and instead small adsorbers can be used which regenerate after each analysis and which therefore do not require replacing, with stoppage of the analyser.

A further aspect of the present invention is the aforesaid analyser, further characterised in that the catalytic combustion reactor is in three stages, of which the first stage is a combustion chamber and a collection zone for the ashes which can be easily removed by the use of a retractable quartz insert; the second stage is a catalytic bed for high temperature combustion of organic vapour; the third stage is a catalytic bed suited to oxidation at lower temperatures, enabling complete combustion of possible traces which have only partially combusted.

A further aspect of the present invention is one of the aforesaid analysers, further characterised in that:

the reduction reactor is in two stages, whereby in the first stage the catalytic bed consists of metallic copper to enable the reduction of $NO_X$ to nitrogen and to absorb excess oxygen, and the second stage contains a catalytic bed of copper oxide to enable oxidation of traces of CO to $CO_2$. With the three-stage heterogeneous combustion reactor, preferably positioned in series with the two-stage reduction reactor, the presence of the partial oxidation product of carbon, i.e. carbon monoxide, is almost completely eliminated, and at the same time the small excess of oxygen inside the gas lines of said analyser is also reduced.

A further aspect of the present invention is one of the aforesaid nitrogen analysers, characterised in that the water absorber comprises:

a moisture exchanger towards the outside, consisting of a tube of a suitable polymer lapped in a counter current direction by dry gases conveyed from all the emissions leaving the instrument, a microfilter of a substance able to adsorb possible traces of non evaporated water.

This system again avoids the use of traps containing large quantities of water adsorbent substances, able to cause considerable pressure drops in the gaseous fluid to be analysed.

DESCRIPTION OF THE FIGURES

FIG. 2 shows a schematic side view of the $CO_2$ adsorption device of the analyser of the present invention.

FIG. 2A shows a schematic view of the $CO_2$ adsorption device of the present invention taken from above.

DETAILED DESCRIPTION OF THE INVENTION

Further advantages attainable with the nitrogen analyser of the present invention will be more evident to the person skilled in the art from the following detailed description of a particular embodiment thereof shown in said figures.

Figure 1:
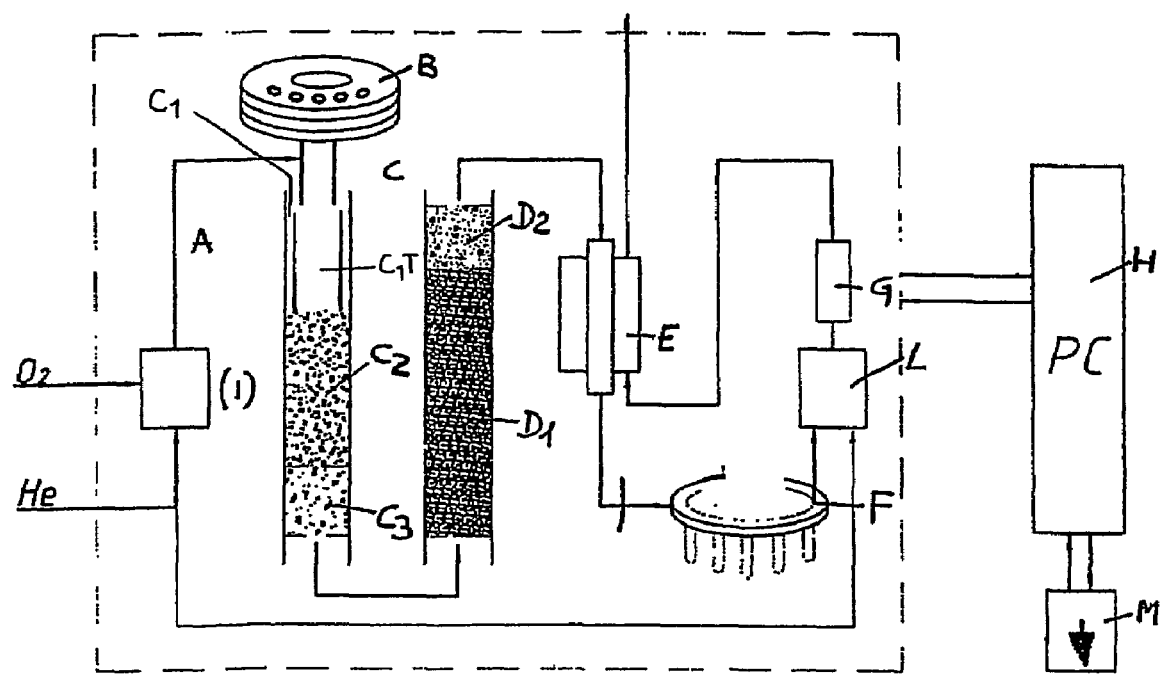
FIG. 1 represents a flow sheet of a preferred embodiment of the analyser of the present invention.

FIG. 1 shows a flow diagram of a preferred embodiment of the nitrogen analyser of the present invention.

In this figure A indicates the gas lines through which helium and oxygen pass upstream of the heterogeneous combustion reactor, while $CO_2$, $N_2$, water and helium, i.e. the carrier gas, pass downstream of the reduction reactor, only nitrogen and helium passing upstream of the detector.

In said figure, B indicates an automatic sampler preferably of 120 positions, consisting of three superposed carousels each comprising 40 positions.

The sampler is operated by a pneumatic device, which while allowing a sample to fall into the combustion reactor, simultaneously loads the next sample onto a piston-operated slide in the interior of the sampler. Oxygen and helium are also fed into the system via the sampler.

In said FIG. 1 the heterogeneous combustion reactor is indicated by C, its first stage consisting of a combustion chamber and ash accumulation zone being indicated by C1, and the extractable quartz tube contained in C1 being indicated by C1T. The second stage containing a suitable catalytic bed in which the fast oxidation reaction at high temperature takes place is indicated by C2. Finally the third stage, i.e. that of the slower oxidation reaction, is indicated by C3.

The catalysts used for the catalytic beds of the first stage and second stage are generally those which are already known and habitually used in fast and slow heterogeneous gas phase oxidation reactions respectively.

According to a particularly preferred embodiment, both stages use mixed oxide spinels (oxygen pump) preferably based on Cr/Co for the first stage and preferably based on Cr/Cu for the second stage, both supported on identical supports preferably consisting of alumina but of different surface area, preferably about 6 $m^2/g$ for the first stage and about 50 $m^2/g$ for the second stage.

The reduction reactor is indicated by the letter D, D1 indicating the first stage in which $NO_x$ is reduced to nitrogen, this stage being conducted in the presence of metallic copper of high surface area (about 0.4 $m^2/g$) which enables both the excess oxygen and impurities consisting of S or halogens to be retained, the second stage D2 consisting of a catalytic bed of copper oxide being used for oxidising traces of CO to $CO_2$.

The water absorber is indicated by the letter E, as aforestated, and comprises a moisture exchanger towards the outside, consisting of a tube lapped in counterflow by dry gases conveyed from all the exit emissions from the instrument.

Preferably, in the analyser of the present invention the water adsorbing device uses moisture exchangers of the ME® series manufactured by Permapure, these being NAFION® membrane tubes.

The microfilter, of a substance capable of adsorbing any traces of unevaporated water and positioned at the exit of the water adsorber, preferably consists of magnesium perchlorate.

F indicates the $CO_2$ adsorber device, which will be examined in detail in the course of the present description, and G indicates the detector, which is preferably an absolute electroconductivity detector, which therefore does not require a flow of reference gas, but is based on the energy developed by a filament maintained at constant temperature by being lapped by a gas of constant flow rate.

H indicates the logic unit for data processing.

Said preferred embodiment also comprises a device for verifying the stability of the primary flow, it being indicated by I in FIG. 1 and consisting of a flow sensor and a metering valve for controlling any pressure increases within the line A situated upstream of the combustion reactor while metering oxygen during the actual combustion stage.

The same preferred embodiment also comprises a device for verifying the stability of the secondary flow, it being situated downstream of the $CO_2$ absorber and indicated by L in FIG. 1. This device also consists of a flow sensor and a metering valve for controlling any pressure fall within the line A caused by the elimination of excess oxygen, carbon dioxide and finally water, in order to stabilise the detector G.

In the preferred embodiment shown in FIG. 1, the analyser of the present invention comprises both the device I for verifying the stability of the primary flow and the device L for verifying the stability of the secondary flow.

The preferred embodiment shown in FIG. 1 also shows that a sample weighing system M is connected to the logic unit H for data processing.

FIG. 2 shows a preferred embodiment of the $CO_2$ absorption device of the nitrogen analyser of the present invention, where F2 indicates the carousel consisting of a plurality of absorber elements 1008 containing an adsorbent material, and F3 indicates the degassing furnace.

According to a particularly preferred embodiment, the elements 1008 are U-shaped glass tubes.

Figure 3:
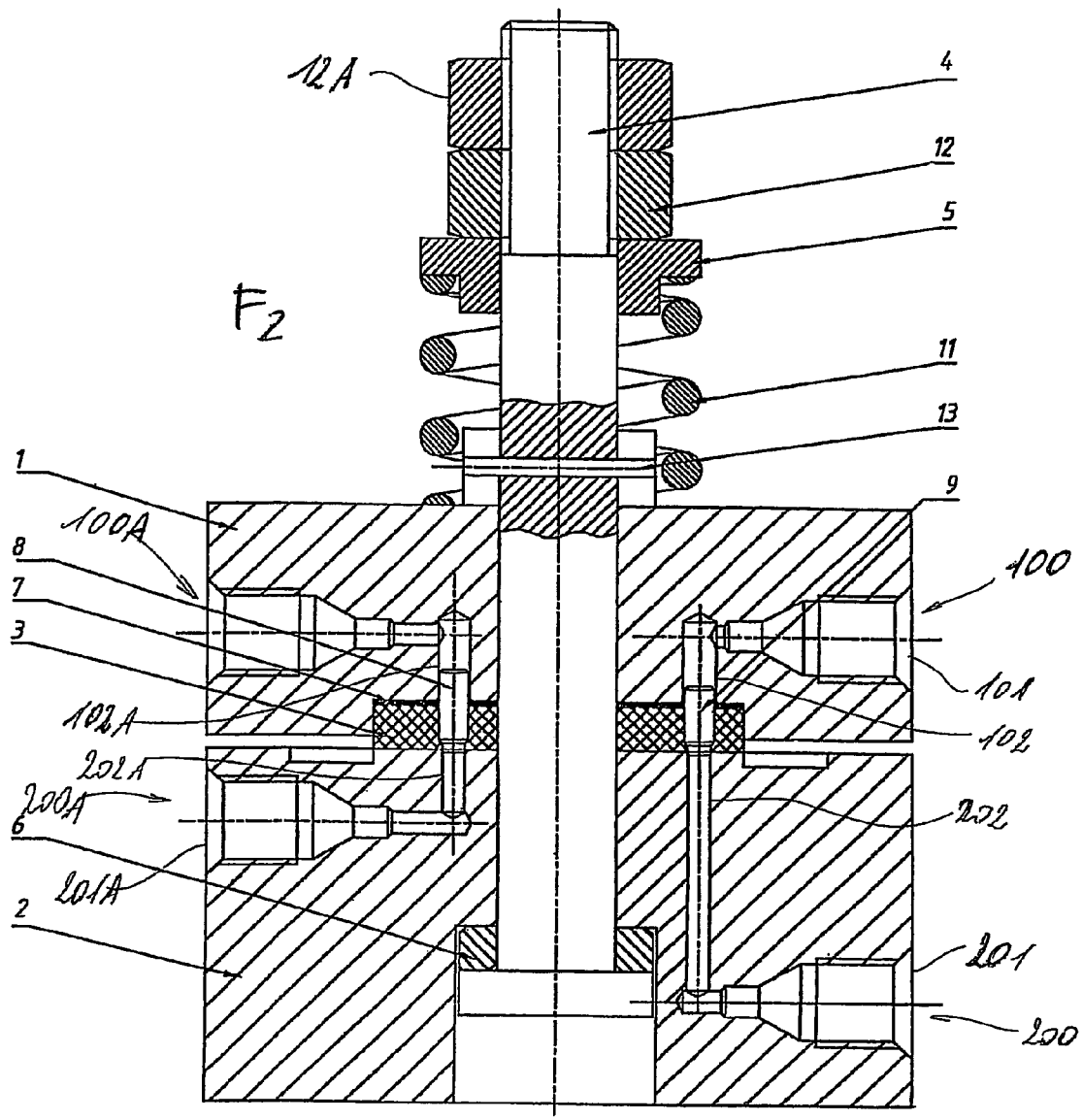
FIG. 3 shows a schematic side sectional view of an example of a gaseous fluid distributor valve contained in the $CO_2$ adsorption device in the nitrogen analyser of the present invention.

The distributor valve indicated by F1 in FIG. 2 comprises, as can be seen from FIG. 3, a shaft 4, an upper body 1 and a lower body 2 both pivoted on the shaft 4. A washer 3, preferably of polytetrafluoroethylene, and an overlying gasket 7, preferably of silicone rubber, are interposed between the lower body 2 and upper body 1.

A compression and adjustment spring 11, a washer 6, an adjustment nut 12, a backing nut 12A and an adapting washer 5, interposed between the adjustment nut 12 and the compression spring 11, are also mounted on the shaft 4.

Figure 3A:
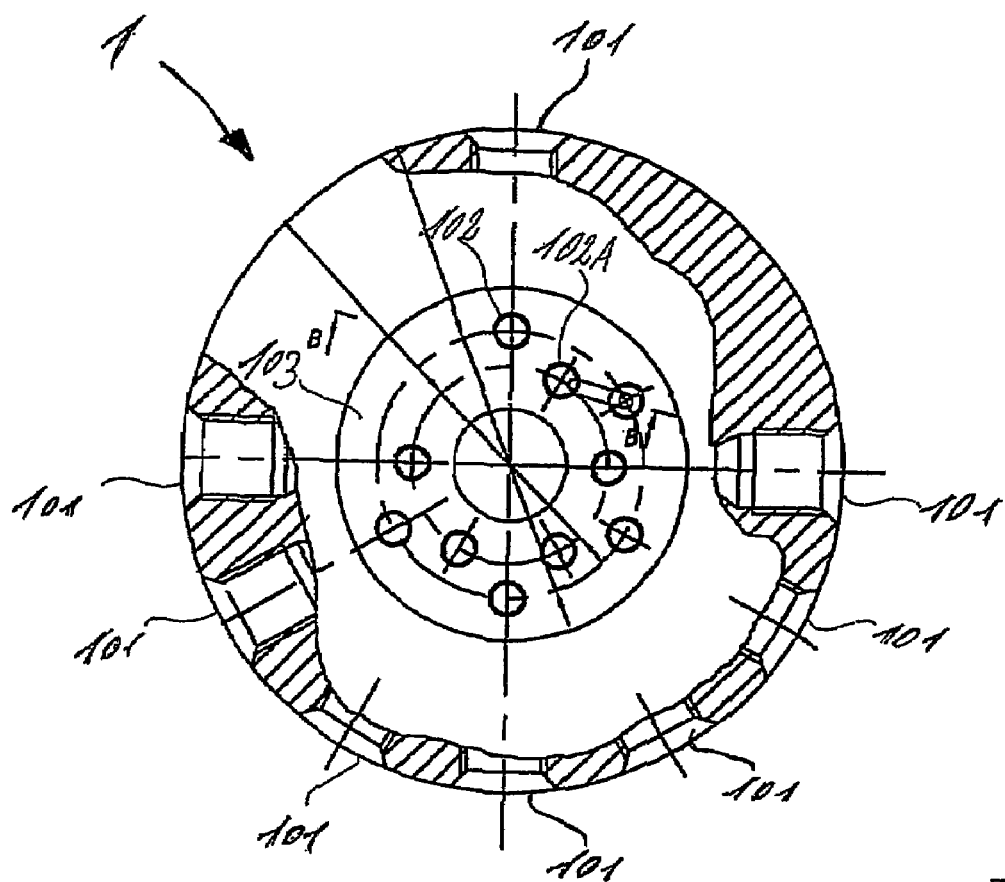
FIG. 3A shows a schematic plan view of the upper body of the valve of FIG. 3.
Figure 3B:
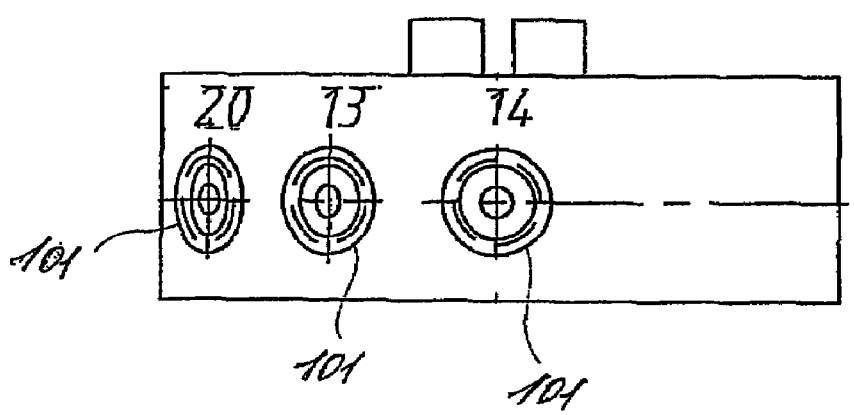
FIG. 3B shows a schematic side view of the upper body of the valve of FIG. 3.
Figure 4A:
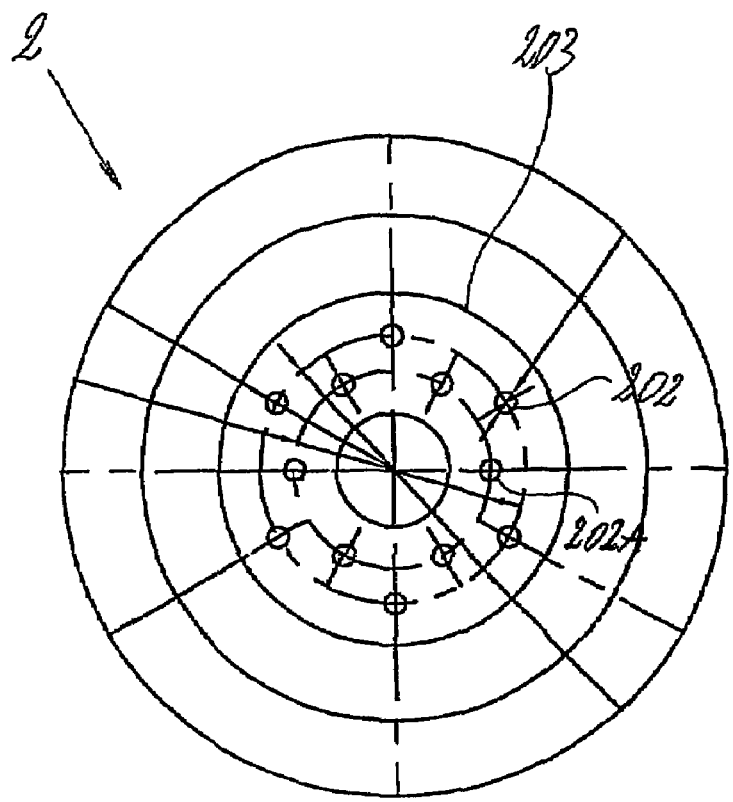
FIG. 4A shows a schematic plan view of the lower body of the valve of FIG. 3.

The gasket 7 and the washer 3 are partially inserted into a seat 103—FIG. 3A—provided in the inner flat face of the upper body 1; the gasket 7 also rests against a resting surface at the circular ring 203—FIG. 4A—provided on the inner flat face of the lower body 2 and substantially concentric with the shaft 4, so that there is no direct contact between the lower body 2 and the upper body 1, and the compression force of the spring 11 is transmitted between the lower body 2 and the upper body 1 substantially only via the gasket 7 and the washer 3.

The compression spring 11 and the washer 6 enable the lower body 2 and upper body 1 to discharge onto the washer 3 and gasket 7 the compressing force exerted by said spring 11, to pack and compress together all four said elements.

The compression force of the spring 11 is adjusted by the nut 12, whereas the washer 5 correctly distributes the reaction force of the nut 12 on the spring 11.

As shown in FIGS. 2, 2A, 3, 3A and 3B, inside the upper body 1 there are excavated a plurality of conduits 100 and 100A connected via an opening 101 and 101a respectively, to the inlet and outlet tubes T1, T2, T3 and T4 for the carrier gas helium which at the appropriate time convey the combustion products to the detector, and the $CO_2$ during degassing.

The conduits 100 also present an opening 102 and 102A in the seat 103 provided in the inner flat face of the upper body 1.

Figure 4B:
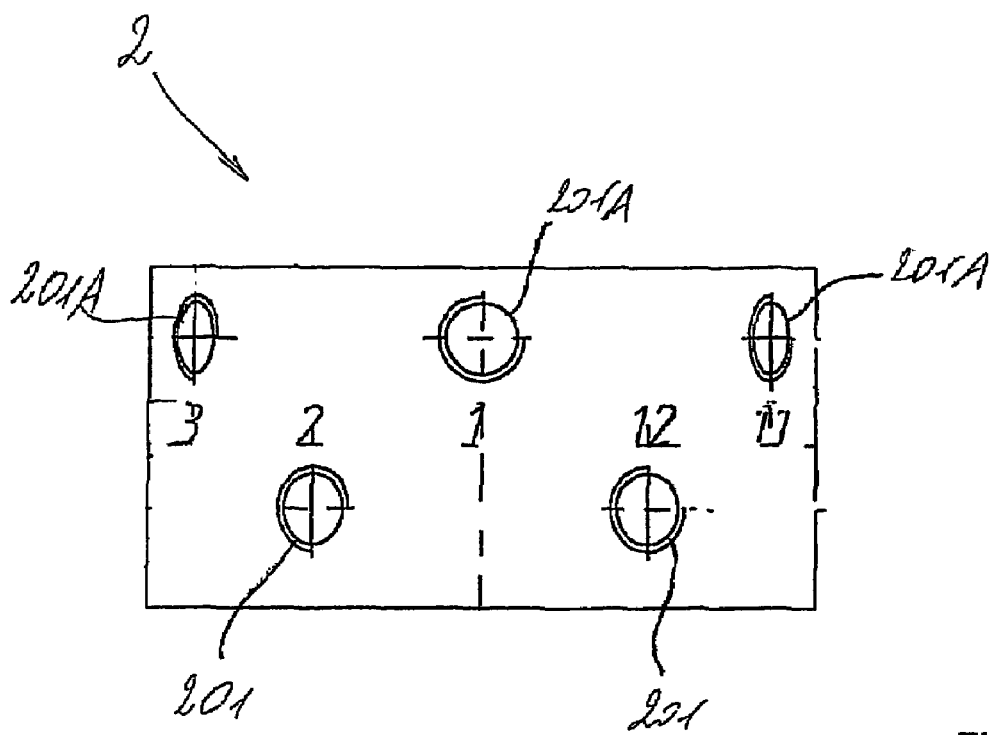
FIG. 4B shows a schematic side view of the lower body of the valve of FIG. 3.

In a similar manner in the embodiment of FIGS. 3, 4A, 4B, inside the lower body 2 the conduits 200, 200A each present a first opening 201, 201A in the cylindrical side wall of the lower body 2. Each pair of conduits 200 and 200A are connected via said openings 201 and 201A to the adsorber element 1008 forming part of the carousel F2. The conduits 200 and 200A also present an opening 202 and 202A at the circular ring shaped resting seat 203 provided on the inner flat face 203 of the lower body 2.

The conduits 200, 200A provided in the lower body 2 are preferably 12 in number, equidistant one to another at an angle of 30° to the axis of the shaft 4: in this manner on rotating the lower body 2 about the upper body 1 by 30°, the conduit 100 is put into communication with the conduit 200, and the conduit 100A is put into communication with the conduit 200A, as shown in FIG. 3.

Figure 5A:
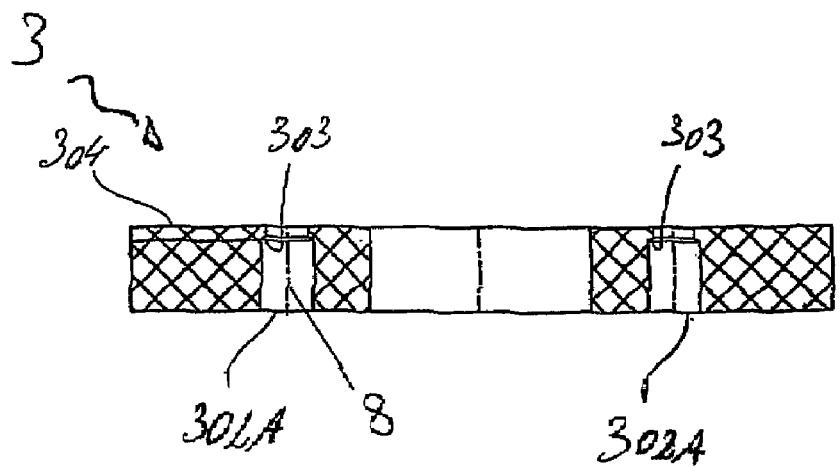
FIG. 5A shows a schematic side view in diametrical section of the valve washer of FIG. 2.

At each opening 102, 102A, between the washer 3, the gasket 7 and the upper body 1 there is interposed a tube 8, shown in FIGS. 3 and 5A.

Figure 5:
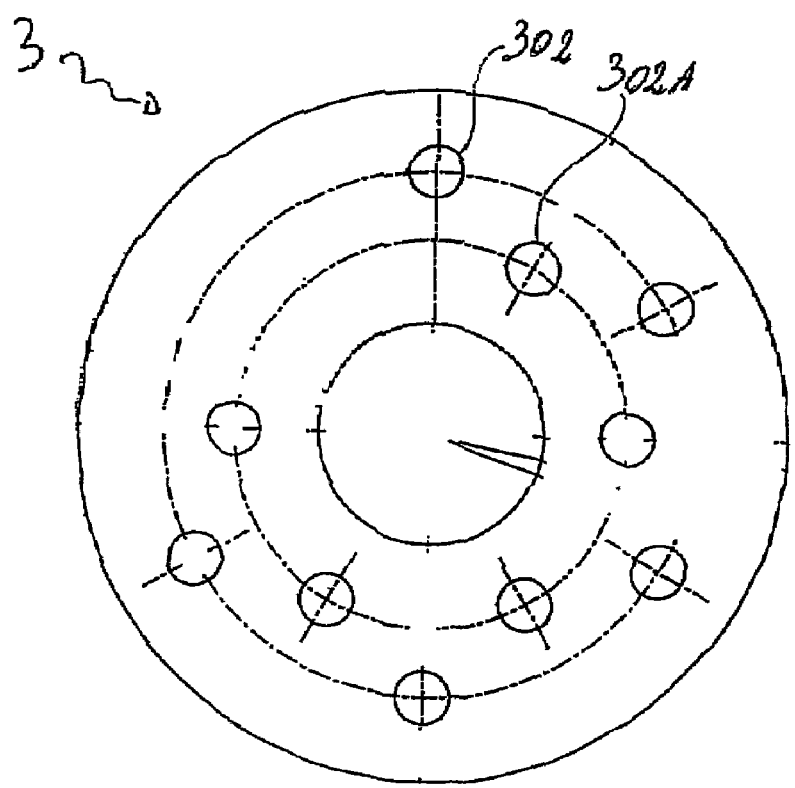
FIG. 5 shows a schematic plan view of the valve washer of FIG. 2.
Figure 6:
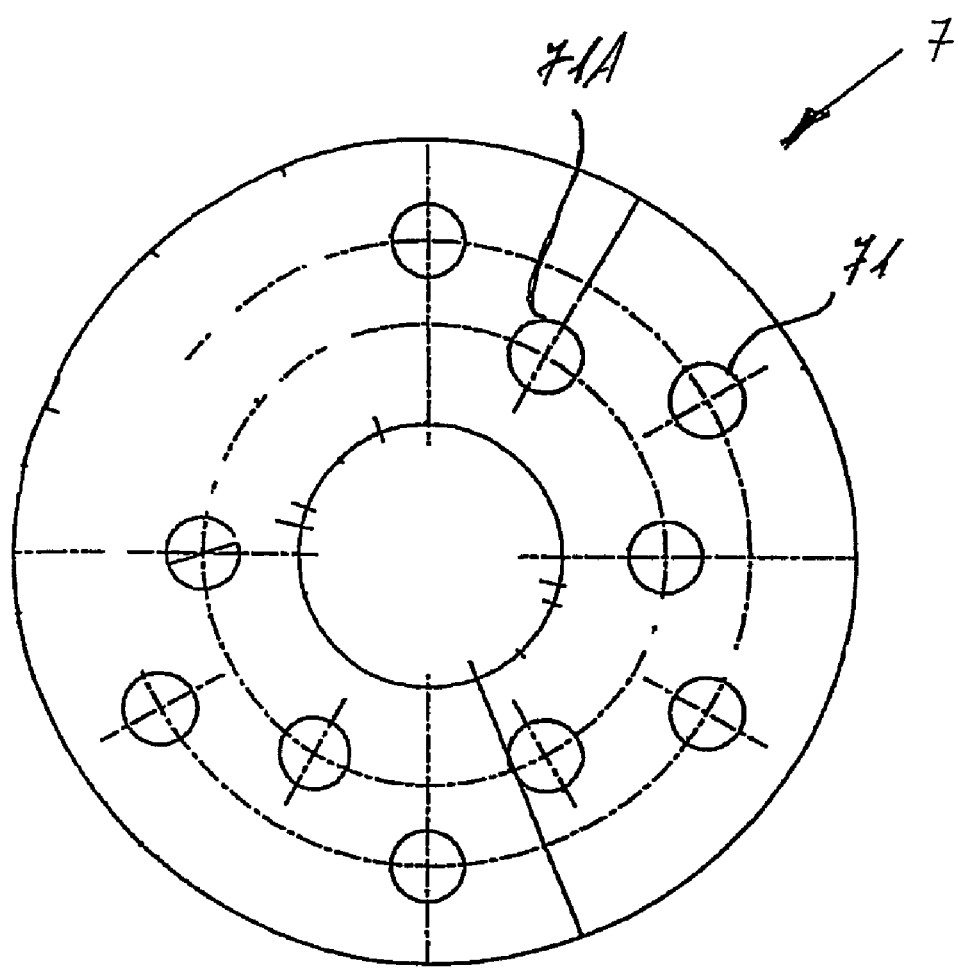
FIG. 6 shows a schematic plan view of the valve gasket of FIG. 2.
Figure 6A:
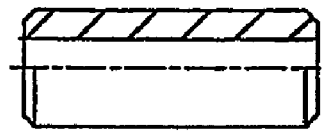
FIG. 6A shows a partly sectional schematic side view of a tube 8 of the valve of FIG. 3.

Each tube 8 is inserted with slight clearance, preferably with a radial gap variable between 0.2 mm and 0.4 mm, into an opening 102 or 102A of the upper body 1 and into each hole 71, 71A of the rubber gasket 7 (FIG. 6). Each tube is also inserted with slight radial interference, for example 0-0.05 mm, into each hole 302, 302A of the washer 3 (FIGS. 5 and 5A).

A small shoulder 303 (FIG. 5A) on the washer 3 maintains each tube 8 separated and at a certain distance from the lower body 2, so as not to slide against it during rotation of the valve. In addition to making the gasket 7 and washer 3 rigid with the upper body 1, so as to prevent undesirable slippage between said components, the tubes 8 provide a good seal for the distributor valve against gas seepage, and in fact prevent seepage between the different gas paths defined by the different pairs of conduits 100, 200, 100A, 200A: in this respect the sufficiently soft silicone rubber gasket 7 when compressed by the spring 11 widens laterally and grips the outer surface of the tubes 8, to ensure a good seal against seepages.

The invention claimed is:

1. An automatic analyser, by way of combustion, for the determination of nitrogen in organic compounds, in particular proteins present in foods, animal feeds, polymers, fuel, comprising:
   lines for gaseous fluids (A)
   sample holders for analysis (B)
   catalytic combustion reactor (C)
   reduction reactor (D)
   water adsorber (E)
   $CO_2$ adsorber (F)
   nitrogen detector (G)
   logic unit for processing the determined data (H),
   wherein the device for absorption of carbon dioxide located upstream of the nitrogen detector, is self regenerating and comprises:
   a distributor valve (F1) able to switch different gas circuits without contaminations and losses from one gas sample to another,
   a carousel (F2) consisting of a plurality of adsorber elements (1008) inside which is placed an adsorbent material, each of the aforesaid elements presenting itself in turn for each analysis, wherein the elements (1008) are U-shaped glass tubes,
   a furnace (F3) able to regenerate, by means of degassing, each of the aforesaid adsorbers in turn, they being conveyed therein at the end of said analysis.

2. An analyser as claimed in claim 1, wherein the combustion reactor (C), is in three stages, of which the first stage (C1) consists of a combustion chamber and ash accumulation zone by the use of an extractable quartz insert (C1T), the second stage (C2) consists of a catalytic bed for high temperature combustion of organic vapours, the third stage (C3) consists of a catalytic bed suitable for oxidation at lower temperature and enables the combustion of possible traces, which have only partially combusted, to be completed.

3. An analyser as claimed in claim 1, wherein the reduction reactor (D) is in two stages, whereby in the first stage (D1) the catalytic bed consists of metallic copper to enable reduction of $NO_x$ to nitrogen and to absorb excess oxygen, while the second stage (D2) contains a catalytic bed of copper oxide to enable the oxidation of traces of CO to $CO_2$.

4. An analyser as claimed in claim 1, wherein the water adsorber (E) comprises:
- a moisture exchanger towards the outside consisting of a tube of suitable polymer lapped in counterflow by dry gases conveyed from all the exit emissions from the instrument
- a microfilter of a substance able to adsorb any traces of unevaporated water.

5. An analyser as claimed in claim 1, wherein the sample holder is an automated sampler of 120 positions, consisting of three superposed carousels each comprising 40 positions and is operated by a pneumatic device, which while allowing a sample to fall into the combustion reactor, simultaneously loads the next sample onto a piston operated slide in the interior of the sampler.

6. An analyser as claimed in claim 2, wherein for both heterogeneous combustion stages of the reactor (C) mixed oxide spinels based on Cr/Co are used for the first stage and based on Cr/Cu are used for the second stage, both supported on alumina with a surface area of about 6 $m^2/g$ for the first stage and about 50 $m^2/g$ for the second stage.

7. An analyser as claimed in claim 3, wherein the first stage (D1) of the reduction reactor (D) also enables impurities consisting of S and halogens to be retained.

8. An analyser as claimed in claim 1, wherein the detector (G) is of absolute electroconductivity type.

9. A nitrogen analyser as claimed in claim 1, also comprising a device (I) to verify the stability of the primary flow, consisting of a flow sensor and a metering valve for controlling any pressure increases within the line (A) situated upstream of the combustion reactor in the oxygen metering step and during the combustion step.

10. An analyser as claimed in claim 1, also comprising a device to verify the stability of the secondary flow (L) situated downstream of the $CO_2$ adsorber, consisting of a flow sensor and a metering valve for controlling any vacuum within the line (A), caused by the elimination of excess oxygen and carbon dioxide, with the aim of stabilising the detector (G).

11. An analyser as claimed in claim 9, also comprising a device to verify the stability of the secondary flow (L) situated downstream of the $CO_2$ adsorber, consisting of a flow sensor and a metering valve for controlling any pressure ball within the line (A), caused by the elimination of excess oxygen and carbon dioxide, with the aim of stabilising the detector (G).

12. An analyser as claimed in claim 1, wherein a sample weighing system (M) is connected to the logic unit (H) for data processing.

13. An analyser as claimed in claim 1, wherein the valve F1 comprises a shaft 4, an upper body (1) and a lower body (2) both pivoted on the shaft (4), with a gasket (7) and a washer (3) interposed respectively.

14. An analyser as claimed in claim 13, wherein the washer (3) is of PTFE.

15. An analyser as claimed in claim 13, wherein the gasket (7) is of silicone rubber.

16. An analyser as claimed in claim 13, wherein a compression and adjustment spring (11), a washer (6), an adjustment nut (12), a backing nut (12A) and an adapting washer (5), interposed between the adjustment nut (12) and the compression spring (11), are also mounted on the shaft (4).

17. An analyser as claimed in claim 13, wherein inside the upper body (1) there are excavated a plurality of conduits (100) and (100A) connected via an opening (101) and (101A) respectively, to the inlet and outlet, tubes (T1), (T2), (T3) and (T4) for the carrier gas helium, which at the appropriate time convey the combustion products to the detector and the $CO_2$ during degassing, said conduits (100) and (100A) also presenting an opening (102) and (102A) in the seat (103) provided in the inner flat face of the upper body (1).

18. An analyser as claimed in claim 13, wherein inside the lower body (2) the conduits (200) and (200A) each present a first opening (201), (201A) in the cylindrical side wall of the lower body (2), each pair of conduits (200) and (200A) being connected via said openings (201) and (201A) to the adsorber element (1008) forming part of the carousel (F2), said conduits (200) and (200A) also presenting an opening (202) and (202A) at the circular ring shaped resting seat (203) provided on the inner flat face (203) of the lower body 2.

19. A nitrogen analyser as claimed in claim 18 wherein the conduits (200) and (200A) provided in the lower body (2) are preferably 12 in number, equidistant one from another at an angle of 30° to the axis of the shaft (4): in this manner on rotating the lower body (2) about the upper body (1) by 30°, the conduit (100) is put into communication with the conduit (200), and the conduit (100A) is put into communication with the conduit (200A).

20. An analyser as claimed in claim 16, wherein at each opening (102), (102A), a tube (8) is interposed between the washer (3), the gasket (7) and the upper body (1).

21. A nitrogen analyser as claimed in claim 20, wherein a small shoulder (303) on the washer (3) maintains each tube (8) separated and at a certain distance from the lower body (2), so as not to slide against it during rotation of the valve.

* * * * *